United States Patent [19]
Murray

[11] Patent Number: 5,905,142
[45] Date of Patent: May 18, 1999

[54] PROTEASE RESISTANT PDGF AND METHODS OF USE

[75] Inventor: Mark J. Murray, Seattle, Wash.

[73] Assignee: ZymoGenetics, Inc., Seattle, Wash.

[21] Appl. No.: 08/436,140

[22] Filed: May 8, 1995

Related U.S. Application Data

[62] Division of application No. 08/303,594, Sep. 9, 1994, which is a continuation of application No. 07/557,219, Jul. 23, 1990, abandoned.

[51] Int. Cl.⁶ .............................. C12N 15/18; C07K 14/49
[52] U.S. Cl. ............................................ 530/399; 530/350
[58] Field of Search ........................ 530/350, 399; 514/12; 435/69.1, 69.4

[56] References Cited

U.S. PATENT DOCUMENTS

| | | | |
|---|---|---|---|
| 4,845,075 | 7/1989 | Murray et al. | 514/12 |
| 5,045,633 | 9/1991 | Murray et al. | 530/399 |
| 5,512,545 | 4/1996 | Brown et al. | 514/12 |

FOREIGN PATENT DOCUMENTS

| | | | |
|---|---|---|---|
| 0 177 957-A2 | 4/1986 | European Pat. Off. | C12N 15/00 |
| 0 177 957-A3 | 4/1986 | European Pat. Off. | C12N 15/00 |
| 0 259 632-A1 | 3/1988 | European Pat. Off. | C12N 15/00 |
| 0 282 317-A2 | 9/1988 | European Pat. Off. | C07K 13/00 |
| 90/04035 | 4/1990 | WIPO | C12N 15/00 |

OTHER PUBLICATIONS

Johnsson et al., "The c–*sis* gene encodes a precursor of the B chain of platelet–derived growth factor," *EMBO J.* 3(5):921–928, 1984.

Betsholtz, et al., "cDNA sequence and chromosomal localization of human platelet–derived growth factor A–chain and its expression in tumour cell lines," *Nature* 320:695–699, 1986.

*Primary Examiner*—Marianne P. Allen
*Attorney, Agent, or Firm*—Townsend and Townsend and Crew LLP

[57] ABSTRACT

PDGF B-chain polypeptides characterized by the substitution or deletion of a lysine or arginine residue at position 27, 28, 32, 79, 80 or 81 of native B-chain are disclosed. Also disclosed are PDGF-like proteins containing the B-chain polypeptides. The polypeptides and proteins may be produced through the use of cultured cells transfected or transformed to express DNA molecules that encode the polypeptides. The PDGF-like proteins are useful as components of cell culture media and for accelerating the healing of wounds.

15 Claims, 4 Drawing Sheets

FIG. 1

```
B CHAIN
  1           10          20          30
  SLGSLTIAEPAMIAECKTRTEVFEISRRLIDRTN
         SIEEAVPAVCKTRTVIYEIPRSQVDPTS
         1           10          20   25
  A CHAIN 35        40          50          60          70
  ANFLVWPPCVEVQRCSGCCNNRNVQCRPTQVQLRPVQV
  ANFLIWPPCVEVKRCTGCCNTSSVKCQPSRVHHRSVKV
  30          40          50          60

80          90          100         109
  RKIEIVRKKPIFKKATVTLEDHLACKCETVAAARPVT
  AKVEYVRKKPKLKEVQVRLEEHLECACATTSLNPDYRE
          70          80          90        100  104
```

PROTEASE RESISTANT PDGF AND METHODS OF USE

CROSS-REFERENCE TO RELATED APPLICATION

This application is a division of U.S. patent application Ser. No. 08/303,594, filed Sep. 9, 1994; which was a continuation of U.S. patent application Ser. No. 07/557,219, filed Jul. 23, 1990, now abandoned.

TECHNICAL FIELD

The present invention relates to the production of platelet-derived growth factor-like proteins, and to the use of those proteins in enhancing the wound-healing process in warm-blooded animals.

BACKGROUND OF THE INVENTION

Human platelet-derived growth factor (PDGF) has been shown to be the major mitogenic protein in serum for mesenchymal-derived cells. This is well documented by numerous studies showing induction of either cell multiplication or DNA synthesis (a prerequisite for cell division) in cultured smooth muscle cells, fibroblasts and glial cells by platelet-rich plasma or purified PDGF (Ross et al., *Proc. Natl. Acad. Sci U.S.A* 71:1207, 1974; Kohler and Lipton, *Exp. Cell Res.* 87:297, 1974; Westermark and Wasteson, *Exp. Cell. Res.* 98:170, 1976; Heldin et al., *J. Cell Physiol.* 105:235, 1980; Raines and Ross, *J. Biol. Chem.* 257:5154, 1982). Furthermore, PDGF is a potent chemoattractant for monocytes and for cells that are responsive to it as a mitogen (Grotendorst et al., *J. Cell Physiol.* 113:261, 1982; Seppa et al., *J. Cell Biol.* 92:584, 1982). PDGF has also been reported to be a chemoattractant for neutrophils. Due to its mitogenic activity, PDGF is useful as a component of a defined medium for the growth of mammalian cells in culture and as a research reagent with multiple applications in the study of animal cell biology.

In vivo, PDGF normally circulates stored in the alpha granules of platelets. Injury to arterial endothelial linings causes platelets to adhere to the exposed connective tissue and release their granules. The released PDGF is thought to chemotactically attract fibroblasts, smooth muscle cells and monocytes/macrophages to the site of injury and to induce the focal proliferation of fibroblasts and smooth muscle cells as part of the process of wound repair (Ross and Glomset, *N. Eng. J. of Med.* 295:369, 1976). PDGF is also produced by a number of other cell types, including endothelial cells.

PDGF has been demonstrated to be an effective wound-healing agent in several animal models of wound healing (Murray et al. U.S. patent application Ser. No. 07/230,190; Thomason et al., EP 282,317; Greenhalgh et al., *Am. J. Pathol.* 136:1235–1246, 1990) and has been used in combination with insulin-like growth factor 1 (IGF-1) to promote bone healing (U.S. Pat. No. 4,861,757) and in combination with transforming growth factor alpha (U.S. Pat. No. 4,874,746).

It has been postulated that as a part of the response to injury of the arterial wall, PDGF released by platelets may play a causative role in the development of the proliferative lesions of atherosclerosis (Ross and Glomset, ibid.), which is one of the principal causes of myocardial and cerebral infarction.

Natural PDGF may be isolated from human plasma or platelets as starting material, but this is a complex and expensive process, in part due to the limited availability of the starting material. In addition, it is laborious to purify PDGF by classical methods at a high yield from other serum components due to its extremely low abundance and biochemical properties. Furthermore, the therapeutic use of products derived from human blood carries the risk of disease transmission due to contamination by, for example, hepatitis virus, cytomegalovirus, or HIV.

PDGF can now be produced by recombinant DNA techniques (U.S. Pat. Nos. 4,766,073; 4,769,328,; 4,801,542; 4,845,075 and 4,849,407), thus overcoming the cost and risk of contamination associated with its isolation from plasma or platelets. However, both the native and recombinant forms of PDGF exhibit amino-terminal sequence heterogeneity, indicating that the molecule is sensitive to proteolysis. Such heterogeneity can interfere with product uniformity and may therefore be undesirable in a therapeutic compound.

In view of PDGF's clinical applicability in the treatment of injuries in which healing requires the chemoattraction and proliferation of fibroblasts or smooth muscle cells and its value as an important component of a defined medium for the growth of mammalian cells in culture, the production of useful quantities of protein molecules with activities comparable to those of native PDGF is clearly invaluable. There is therefore a need in the art for compositions of biologically active PDGF-like proteins that are resistant to proteolysis and therefore more homogeneous. The present invention provides such proteins and further provides other, related advantages.

SUMMARY OF THE INVENTION

Briefly stated, the present invention provides PDGF B-chain polypeptides characterized by a substitution or deletion at an amino acid position selected from the group consisting of position 27, position 28, position 32, position 79, position 80 and position 81 of native B-chain. Within preferred embodiments, the polypeptides contain an amino acid selected from the group consisting of proline, serine, tryptophan, glutamine, histidine, methionine and asparagine at one or more of these positions.

A related aspect of the present invention provides PDGF-like proteins comprising a first PDGF B-chain polypeptide as disclosed above, wherein the B-chain polypeptide is disulfide bonded to an A-chain polypeptide or another B-chain polypeptide.

In another aspect, the present invention provides DNA molecules encoding the PDGF B-chain polypeptides disclosed above, as well as cultured cells transfected or transformed to express the DNA molecules. The DNA molecules and cells are useful within methods for producing PDGF-like proteins.

These and other aspects of the invention will become evident upon reference to the following detailed description and attached drawings.

BRIEF DESCRIPTION OF THE DRAWINGS

FIG. 1 illustrates the amino acid sequences of native human PDGF A-chain and B-chain. Amino acids are represented by the standard one-letter codes.

DETAILED DESCRIPTION OF THE INVENTION

Figure 2:
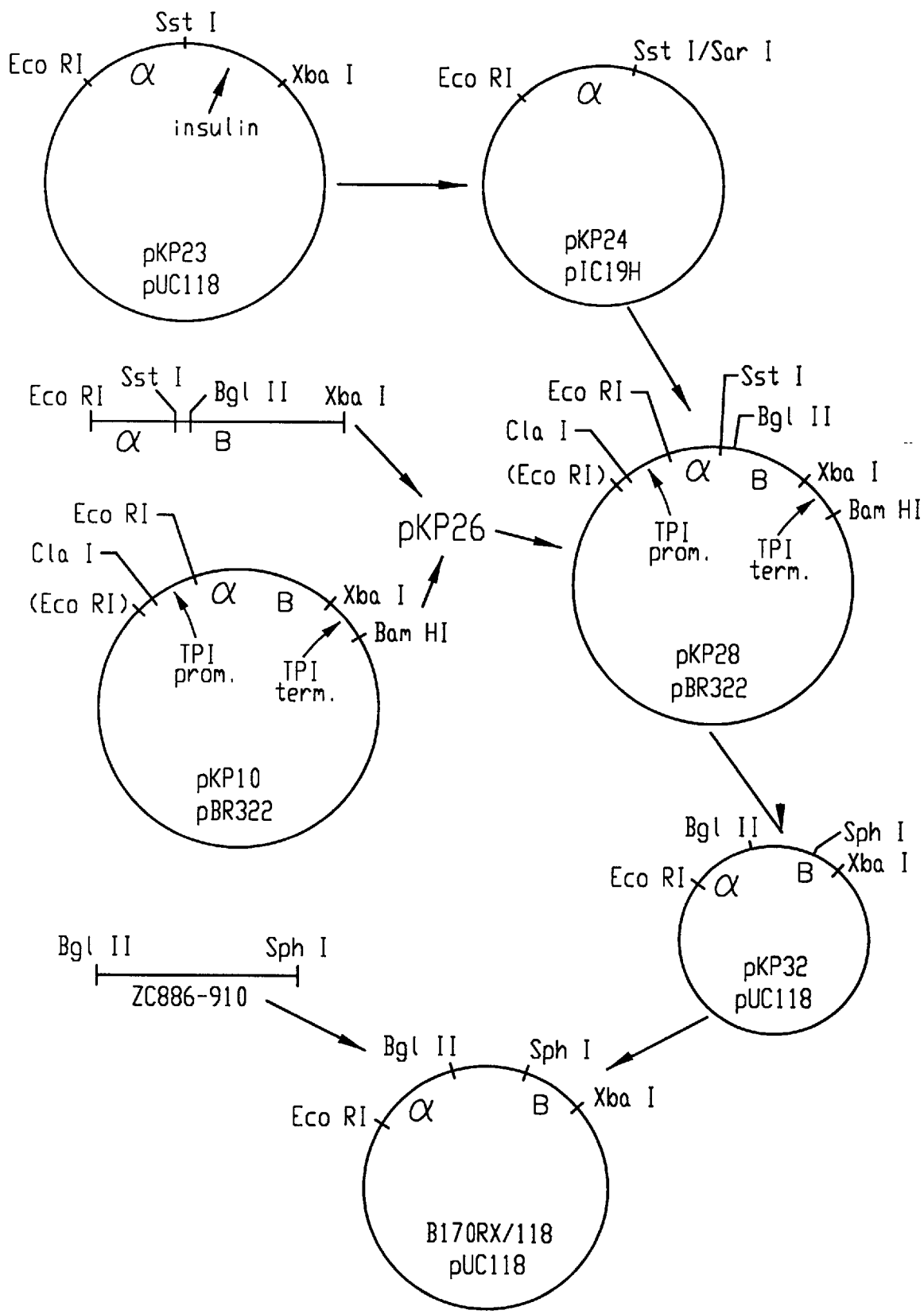
FIG. 2 illustrates the construction of a yeast codon-optimized PDGF B-chain coding sequence.

Prior to setting forth the invention, it may be helpful to an understanding thereof of set forth definitions of certain terms to be used hereinafter.

Polypeptide: A polymer of amino acids.

Complementary DNA: or cDNA. A DNA molecule or sequence which has been enzymatically synthesized from the sequences present in an mRNA template, or a clone of such a molecule.

Secretory Signal Sequence: That portion of a gene or cDNA encoding a secretory peptide. A secretory peptide is the amino acid sequence in a secretory protein which signals its translocation into and transit through the secretory pathway of the cell. Secretory peptides generally occur at the beginning (amino terminus) of the protein and include a stretch of about 9–10 hydrophobic amino acids, although secretory peptides that do not conform to this model have also been identified. Very often the secretory peptide is proteolytically cleaved from the protein during the process of secretion.

Mitogen: A molecule which stimulates cells to undergo mitosis. Mitosis is asexual somatic cell division leading to two daughter cells, each having the same number of chromosomes as the parent cell. Mitosis is typically measured by uptake of $^3$H-thymidine by target cells.

Transformation or transfection: The process of stably and hereditably altering the genotype of a recipient cell or microorganism by the introduction of purified DNA. This is typically detected by a change in the phenotype of the recipient organism. The term "transformation" is generally applied to microorganisms, while "transfection" is used to describe this process in cells derived from multicellular organisms.

Transcription: The process of producing a mRNA template from a DNA coding sequence.

Expression: The process, starting with a structural gene or cDNA, of producing its polypeptide, being a combination of transcription and translation. An expression vector is a plasmid or virus-derived construction designed to enable the expression, in a host cell, of a gene or cDNA carried on the vector.

Transcriptional Promoter: DNA sequences upstream from a gene which promote its transcription.

Biological Activity: Some function or set of activities performed by a molecule in a biological context (i.e., in an organism or an in vitro facsimile). In the case of PDGF, these biological activities include binding to specific call-surface receptors and inducing chemotaxis and/or mitogenesis in responsive cell types. Other biological activities of PDGF may include: phospholipase activation; increased phosphatidylinositol turnover; prostaglandin metabolism; stimulation of both collagen and collagenase synthesis by responsive cells; an indirect proliferative response of cells lacking PDGF receptors; angiogenesis; and potent vasoconstrictor activity.

Native PDGF: PDGF isolated from a natural source, such as platelets. Native human PDGF isolated from platelets has been shown to be a mixture of homodimers and heterodimers of its two component polypeptide chains, termed "A-chain" and "B-chain". As used herein, the terms "homodimer" and "heterodimer" refer to the structure of the newly assembled protein. It will be understood that minor proteolysis may occur subsequent to assembly. This proteolysis may be a result of purification, handling, or analytical procedures, or may result from proteolysis during secretion from a PDGF-producing cell, and may lead to microheterogeneity in the final, purified protein, particularly heterogeneity at the amino terminus of the B-chain. For the purposes of the present invention, the protein is considered a dimer if it is assembled in that form, even though a portion of the molecules may subsequently be cleaved in one or both chains. Due to the disulfide-bonded structure of PDGF dimers, proteolysis of internal peptide bonds may not result in loss of amino acids from the protein, and the overall "dimer" structure is retained despite the loss of one or more peptide bonds.

PDGF-like protein: A disulfide-bonded, dimeric protein, the component chains of which are each at least 80% homologous to one of the component chains of native PDGF, and which exhibits at least one of the biological activities (induction of mitogenesis or chemotaxis in fibroblasts or smooth muscle cells) characteristic of native PDGF.

The present invention provides for the production of PDGF-like protein compositions having enhanced consistency in genetically engineered cultured cells. Suitable host cells include yeast cells, especially *Saccharomyces cerevisiae*, other fungal cell (e.g., Aspergillus), cultured cells from multicellular organisms, such as mammals, insects, fish, birds, etc. and prokaryotic cells. Production of PDGF analogs in eucaryotic cells is generally disclosed by Murray et al. (U.S. Pat. Nos. 4,766,073; 4,769,328; 4,801,542; 4,845,075; 4,849,407 and 4,889,919, which are incorporated herein by reference) and by Thomasen et al., (ibid.). Expression of PDGF in prokaryotic host cells is disclosed by Hoppe et al. (*Biochemistry* 28:2956–2960, 1989).

Native human PDGF was previously postulated to be a heterodimer of related polypeptides designated "A-chain" and "B-chain" (Johnsson et al., *Biochem. Biophys. Res. Comm.* 104:66–74, 1982), or a mixture of A-chain and B-chain homodimers (Johnsson et al., *EMBO J.* 3:921–928, 1984). Recently, PDGF from human platelets has been shown to contain all three isoforms, the AB heterodimer and the AA and BB homodimers (Hart et al., *Biochemistry* 29:166–172, 1990). The component A-chain and B-chain are 56% identical at the amino acid sequence level.

It has been found that recombinant PDGF B-chain is sensitive to proteolysis. Amino acid sequence analysis of recombinant PDGF preparations has shown that the bond between amino acid number 32 (Arg) and amino acid number 33 (Thr) of mature human B-chain is particularly sensitive to proteolysis. The bond between Arg-79 and Lys-80 is also sensitive to proteolysis. (Amino acid numbers used herein refer to the sequence of B-chain shown in FIG. 1.) In addition, the B-chain contains the sequence Arg-Arg at amino acids 27–28, which may be a target of proteolytic attack in some host cell types.

The present invention provides PDGF-like proteins having enhanced protease resistance. Protease resistance is achieved by substitution or deletion of one or more lysine or arginine residues within the potential cleavage sites at Arg(27)-Arg(28), and Arg(32)-Thr(33), and Arg(79)-Lys(80)-Lys(81). In certain preferred embodiments, the arginine residue at position 28 or position 32 is replaced with an amino acid residue other than an arginine or lysine residue, preferably Trp, Ser, Glu, His, Pro, Met, or Asn. In this regard it is most preferred to replace arginine-32 with a proline residue and to replace arginine-28 with serine. Although in principle any amino acid can be substituted for arginine or lysine and the resultant protein readily tested for PDGF biological activity (i.e. chemotactic or mitogenic activity)

and stability, preferred amino acid substitutions may be selected on the basis of chemical and physical similarity or on the basis of homology with the PDGF A-chain. The model of Dayhoff et al. (in *Atlas of Protein Sequence and Structure* 1978, Nat'l. Biomed. Res. Found., Washington D.C.), incorporated herein by reference, may also be used as a guide in selecting candidate amino acid substitutions. The resulting B-chain analog can be assembled into homodimers or, by combining it with PDGF A-chain or an A-chain analog, heterodimers.

The terms "A-chain" and "B-chain" are used herein to denote the predominant forms of these human polypeptides (the sequences of which are shown in FIG. 1), as well as forms containing variations in amino acid sequence that do not significantly alter the essential structure or biological activities of PDGF. Such variations may be due to, for example, genetic polymorphism or may result from human intervention (e.g. directed mutagenesis of cloned sequences). For example, a tyrosine residue may be introduced into the B-chain sequence in place of amino acid number 23 (phenylalanine) to facilitate iodination of the polypeptide. In addition, the cysteine residues at positions 43, 52, 53 and 97 of the native human B-chain and at corresponding positions in A-chain can be replaced with another amino acid, such as serine, without loss of biological activity. It is also possible to truncate the A-chain and B-chain at either or both termini. For instance, up to 15 amino acids can be removed from the amino terminus of the B-chain, and up to 10 amino acids can be removed from the carboxyl terminus of the B-chain. In addition, the B-chain may have, for example, the corresponding sequence encoded by the v-sis gene of simian sarcoma virus, which differs from the predominant human sequence at four positions. Alternative forms of the A-chain having an additional six or nineteen C-terminal amino acids have been inferred from cloned DNA sequences (Tong et al., *Nature* 328:619–621, 1987; Betsholtz et al., *Nature* 320:695–699, 1986).

DNA sequences encoding the component chains of PDGF-like proteins are synthesized according to standard procedures or cloned and altered as necessary by mutagenesis. Methods for introducing amino acid substitutions and deletions by oligonucleotide-directed mutagenesis are well known in the art (reviewed by Sambrook et al., *Molecular Cloning, A Laboratory Manual,* Cold Spring Harbor Laboratory Press, Cold Spring Harbor N.Y., 1989, pages 15.1–15.113).

After a suitable PDGF B-chain DNA is obtained, it is used to produce a recombinant PDGF-like protein. The present invention provides for the production of a variety of PDGF-like proteins, including B-chain homodimers and heterodimers of A-chain and B-chain, as well as dimers containing A-chain and B-chain variants. These proteins include heterodimers containing either the 125-amino acid, the 110-amino acid, or the 104-amino acid A-chain polypeptides. The B-chain components of these dimers are characterized by the deletion or replacement of an arginine or lysine with another amino acid, thereby providing increased protease resistance as compared to the wild-type sequence. These recombinant proteins are assayed for biological activity (e.g. mitogenic or chemotactic activity toward fibroblasts) by any of a variety of assays known in the art as described in more detail below. Protease resistance may be determined by amino-terminal amino acid sequence analysis or polyacrylamide gel electrophoresis under reducing conditions.

PDGF activity (e.g. chemotactic activity) is typically measurable over a greater than 100-fold concentration range. A PDGF-like protein exhibiting 1% of the activity of native PDGF in a standard assay will therefore have detectable activity. Within the present invention, then, a PDGF-like protein is considered to have PDGF biological activity if it exhibits at least 1% of the activity of native PDGF as measured in an in vitro chemotaxis or mitogenesis assay. It is preferred, however, that a PDGF-like protein have at least 10% of the activity of native PDGF.

DNA sequences useful in carrying out the present invention may be obtained from the v-sis gene or from cDNAs encoding the native A-chain or B-chain of PDGF, or suitable sequences may be synthesized according to standard procedures (Murray et al., ibid.) For example, a human A-chain cDNA may be isolated from a human cDNA library made from an appropriate source of messenger RNA by using the v-sis gene or a fragment thereof as a hybridization probe, or through use of oligonucleotide probes designed from the A-chain DNA or amino acid sequence (see, for example, Betsholtz et al., *Nature* 320:695–699, 1986, and Tong et al, *Nature* 328:619–621, 1987). Preferred sources of mRNA include transformed human cell lines, e.g., U2-OS and T-24. These cells can be cultured in vitro and are known to secrete a protein having PDGF-like activity (Heldin et al., *Nature* 319:511–514, 1986). The identity of this cDNA as that encoding A-chain may be verified by DNA sequencing. In a similar manner, a human B-chain cDNA may be isolated from a cDNA library made from an appropriate source of mRNA using the v-sis gene or a fragment thereof as a hybridization probe, or through the use of oligonucleotide probes designed from the B-chain sequence. A preferred source of mRNA in this regard is human umbilical vein endothelial cells. These cells can be cultured in vitro for short periods of time, are known to secrete PDGF (Di Corletto and Bowen-Pope, *Proc. Natl. Acad. Sci U.S.A* 80:1919, 1983) and contain high levels of B-chain mRNA. A human c-sis cDNA clone is disclosed by Clarke et al. (*Nature* 308:464–467, 1984).

A-chain-containing proteins produced according to the present invention may include N-linked carbohydrate or may be free of N-linked carbohydrates. Although the native human A-chain contains a consensus N-linked carbohydrate attachment site, the coding sequence may be modified to remove that site. The consensus glycosylation sequence Asn-X-Ser/Thr is preferably altered to Gln-X-Ser/Thr, although as will be apparent to those skilled in the art, other amino acid sequence changes may be made.

It may be advantageous to employ a fully or partially synthetic coding sequence in order to optimize the codon usage pattern. This is a particular advantage when using microorganism host cells whose codon usage frequencies differ from those of mammals.

Once an appropriate DNA sequence encoding a PDGF polypeptide is obtained, the sequence is ligated to an appropriate transcriptional promoter. In general, the sequence will also be joined to an appropriate transcriptional terminator or polyadenylation signal, depending on the particular host cell chosen. If the sequence is to be expressed in a eukaryotic host and secretion of the polypeptide product is desired, a secretory signal sequence will also be included. The secretory signal sequence may be that of the PDGF A-chain or B-chain, or may be that of another protein, particularly a protein endogenous to the host cell. The resulting expression unit is then inserted into a vector which is used to transfect or transform the selected host cells. Selection of promoters, terminators, leader sequences and vectors appropriate to a specific host cell is within the level of ordinary skill in the art.

Baker's yeast (*Saccharomyces cerevisiae*) cells are a particularly preferred host. Promoters which may be utilized in yeast include the yeast alpha-factor (MFα1) promoter and the yeast triose phosphate isomerase (TPI1) promoter (Kawasaki, U.S. Pat. No. 4,599,311). Promoters may also be obtained from other yeast genes, e.g., alcohol dehydrogenase 1 (ADH1) and alcohol dehydrogenase 2 (ADH2), including variant forms such as the ADH2-4$^c$ promoter (also known as ADR3-4$^c$; Russell et al., *Nature* 304:652–654, 1983; Irani et al., EP 284,044). In yeast, secretion of PDGF-like proteins can be obtained through use of a secretory signal sequence such as the pre-pro sequence of the yeast mating pheromone alpha-factor (Kurjan and Herskowitz, *Cell* 30:933, 1982; Kurjan et al., U.S. Pat. No. 4,546,082; Julius et al, *Cell* 36:309, 1984; and Brake et al, *PNAS* 81:4642, 1984). Other secretion signals may also be used, including the a-factor (Brake, EP 123,289), PHO5 (Le Montt et al., WO 86/00638) SUC2 (Carlson and Botstein, *Cell* 28:145–154, 1982) and BAR1 (MacKay et al., EP 310,137) secretory signal sequences. To ensure the efficient transcription termination and polyadenylation of mRNA, a yeast terminator sequence, such as the TPI1 terminator (Alber and Kawasaki, *J. Molec. Appl. Genet.* 1:419, 1982), is generally included. The expression unit constructions are then inserted into an appropriate expression vector. Expression vectors will generally include an origin of replication and a selectable marker, although integration of the exogenous expression unit into the host genome is within the scope of the present invention. It is preferable to use an expression vector which is stably maintained at a high copy number within the host cell in order to produce more protein per unit of culture. Suitable yeast expression vectors in this regard include the plasmids pCPOT (ATCC 39685), pMPOT2 (Murray et al., ibid.; ATCC 67788) and derivatives thereof, which include the *Schizosaccharomyces pombe* gene encoding the glycolytic enzyme triose phosphate isomerase (POT1 gene). Inclusion of the POT1 gene ensures the stable maintenance of the plasmid in a host cell having a deletion in the triose phosphate isomerase gene when grown in media containing glucose as a carbon source, due to its ability to complement the host cell gene deletion. Other selection systems may also be used, such as the leu2 selection system described by Beggs (*Nature* 275:104–109, 1978).

Expression vectors prepared as described above are then transformed into a yeast host having a genetic defect which can be complemented by the selectable marker. Yeast strains having such defects are widely available, such as from the American Type Culture Collection, Rockville, Md., or the Yeast Genetic Stock Center, Berkeley, Calif., or may be prepared using standard techniques of mutation and selection. It is preferred that the yeast host strain is deficient in vacuolar proteases (e.g. a pep4 mutant). Procedures for transforming yeast are well known in the literature (see, for example, Beggs, ibid. and Hinnen et al, *Proc. Natl. Acad. Sci. U.S.A.* 75:1929–1933, 1978).

The transformed yeast cells may be selected by growth on conventional rich medium containing glucose when a POT1-based vector is utilized. Once selected, transformants containing the appropriate expression constructions are grown to stationary phase, the cells are removed by centrifugation or filtration, and the medium is concentrated. The PDGF-like proteins of the present invention are isolated from the host cells and purified by conventional techniques.

Using a variety of assays, it can be demonstrated that spent media from yeast cultures expressing the PDGF-like proteins of the present invention possess biological activities substantially identical to that of authentic human PDGF.

The PDGF-like proteins of the present invention can also be produced in cultured prokaryotic host cells. The cells are transformed with an expression vector encoding a protease-resistant B-chain. The B-chain is then isolated from the host cells and combined with a second PDGF chain in vitro essentially as disclosed by Hoppe et al. (*Biochemistry* 28:2956–2960, 1989), incorporated herein by reference. Briefly, a PDGF polypeptide is expressed as a fusion protein in *E. coli*. Inclusion bodies are recovered from the cells and solubilized under reducing conditions. The PDGF chain is then isolated from the fusion protein, such as by CNBr cleavage. Thiol groups are protected by S-sulfonation. S-sulfonated chains are then joined by removing the protecting groups with a mixture of reduced and oxidized glutathione in the presence of urea.

Expression of biologically active PDGF-like proteins in eukaryotic cells other than yeast cells can be achieved by a person skilled in the art through use of appropriate expression/regulatory signals. Transcriptional promoters capable of directing the expression of these sequences are chosen for their ability to give efficient and/or regulated expression in the particular eukaryotic cell type. For example, a variety of promoters useful in cultured mammalian host cells are available, including viral (e.g., SV40 and adenovirus) and cellular (e.g., metallothionein gene; U.S. Pat. Nos. 4,601,978 and 4,579,821) promoters. Secretory signal sequences capable of directing the gene product into the cell's secretory pathway are chosen for their function in the particular host cell type. Other useful regulatory signals, such as transcription termination signals, polyadenylation signals and transcriptional enhancer sequences, are also chosen for their function in the host cell, the selection of which would be apparent to an individual skilled in the art. Methods for transforming mammalian cells and expressing cloned DNA sequences therein are described by, for example, Kaufman and Sharp (*J. Mol. Biol.* 159:601–621, 1982), Southern and Berg (*J. Mol. Appl. Genet.* 1:327–341, 1982), Neumann et al. (*EMBO J.* 1:841–845, 1982) and Hagen et al. (U.S. Pat. No. 4,784,950). Methods for expression of cloned genes in cells derived from other higher eucaryotes are disclosed by, for example, Miyajima et al. (*Gene* 58:273–282, 1987), Isa and Shima (*J. Cell Sci.* 88:219–224, 1987) and Kretsovali et al. (*Gene* 58:167–176, 1987). Non-yeast fungi (e.g. Aspergillus and Neurospora spp.) may also be used.

As noted above, according to the present invention it is possible to produce recombinant PDGF-like proteins which are homodimers or heterodimers. Heterodimers may be produced by introducing two different expression units into the same host cell. The expression units may be on different expression vectors with different selectable markers or, preferably, on a single expression vector. The latter strategy offers the advantage of providing equal copy numbers of the two expression units. Heterodimers are isolated from the biologically active products by immobilized metal affinity chromatography (Sulkowski, in *Protein Purification: Micro to Macro,* 149–162, Alan R. Liss, Inc., 1987; Porath et al., *Nature* 258:598, 1975; Hammacher et al., *J. Biol. Chem.* 263:16493–16498, 1988) or immunoaffinity chromatography using isotype-specific monoclonal antibodies as disclosed in U.S. patent application Ser. No. 07/139,960, incorporated herein by reference, using monoclonal antibodies 120.1.2.1.2 (produced from a hybridoma deposited with American Type Culture Collection under accession number HB 9610) and 121.6.1.1.1 (produced from hybridoma ATCC HB 9613) coupled to CNBr-activated Sepharose (Pharmacia, Piscataway, N.J.). The sample is loaded onto an antibody 120.1.2.1.2-Sepharose column, which binds only the BB isoform of PDGF. The antibody 121.6.1.1.1-

Sepharose column is then added in series with the first column (120.12.12-Sepharose) and the sample cycled for 12 hours at 4° C. The latter column binds the AB and BB isoforms of PDGF, but the removal of the BB isoform by the first column (120.1.2.1.2-Sepharose) results in the binding of only AB-dimer material on the second column. The columns are washed in series with PBS (pH 7.2), 0.5M NaCl, and the 121.6.1.1.1 column is eluted with 0.1M glycine, pH 2.5.

For use as mitogenic agents, the proteins of the present invention are isolated and, preferably, purified. For use as therapeutic agents, the proteins will generally be prepared in a substantially pure form, that is, essentially free of other proteins of human or viral origin. Purification can be achieved through the use of standard protein purification techniques, including precipitation, gel filtration, ion exchange chromatography, affinity chromatography, hydrophobic interaction chromatography, etc. Methods for purifying PDGF are disclosed by, for example, Raines and Ross (*J. Biol. Chem.* 257:5154–5160, 1982), Heldin et al. (*Nature* 319:511–514, 1986) and Hart et al. (*Biochemistry* 29:166–172, 1990). For some applications, the isolated or purified PDGF-like proteins will be combined with other proteins (e.g. other growth factors) or non-protein therapeutic agents.

The techniques of cell culture have advanced considerably in recent years as have the number and varieties of mammalian cells which will grow in cultures. Central to these advances is a better understanding of the nutritional requirements (including hormone and growth factor requirements) of cultured cells (Barnes and Sato, *Cell* 22:649, 1980). This understanding permits the formulation of defined, serum-free culture media. The PDGF-like proteins of the present invention are useful as components of these defined media.

The proteins described herein are also suitable for use within therapeutic compositions for enhancing the wound-healing process in warm-blooded animals. The normal wound-healing process in warm-blooded animals proceeds by an orderly series of events involving the interaction of chemoattractants, growth factors, and a variety of specialized cell types. This process includes an ordered migration and, in some cases, the subsequent proliferation of a number of these specialized cell types into the wound space, and involves the complex interaction of a variety of biologically active factors. This process is discussed in detail in Hunt et al., eds., *Soft and Hard Tissue Repair; Biological and Clinical Aspects*, Praeger Publishers, New York, 1984, which is incorporated herein by reference. Briefly, tissue injury results in the release of chemotactic factors which attract particular cell types, which then release additional and/or other chemoattractant or mitogenic factors. These factors, in turn, affect additional specialized cells, ultimately restoring the injured tissue. Further, there is evidence that the rate at which this process normally proceeds is limited by the levels of chemoattractants and growth factors at the wound site, and may be enhanced by the addition of these agents (Grotendorst et al., *J. Clin. Invest.* 76:2323–2329, 1985, herein incorporated by reference).

The proteins of the present invention posses substantially the same biological activity as PDGF isolated from platelets. The basic biological activity of PDGF, particularly the induction of chemotaxis and mitogenesis in responsive cell types (including fibroblasts and smooth muscle cells), underlies many of the physiological roles of this protein, including its role in tissue repair.

The proteins of the present invention are expected to accelerate the healing process in a broad spectrum of wound conditions. For purposes of the present invention, the terms "wound" or "wound condition" include any disruption of the dermal layer of the skin. Examples of disruptions to the dermal layer include chronic non-healing ulcers (which can have a variety of causes), superficial wounds and lacerations, abrasions, surgical wounds, and some burns. In addition, wounds may also result in damage to connective tissue, the repair of which involves fibroblast proliferation and collagen deposition. The proteins of the present invention are of general utility in enhancing the wound-healing process, and are particularly useful in conditions in which the normal wound-healing process is suppressed or inhibited. For example, normal wound-healing may be retarded by a number of factors, including advanced age, diabetes, cancer, poor nutrition and treatment with anti-inflammatory drugs, steroids or anticoagulants, and the proteins described herein may be used to offset the delayed wound-healing effects of such conditions and treatments. These PDGF-like proteins are particularly useful in promoting wound healing in diabetics.

For therapeutic use, the proteins of the present invention are preferably administered topically in combination with a physiologically acceptable carrier or diluent. Further, it is preferable to use a substantially pure preparation of the protein free of impurities or contaminants which would interfere with its therapeutic use. Particularly preferred are those preparations which are free of toxic, antigenic, pyrogenic, inflammatory or other deleterious substances, are are greater than 80% pure, preferably greater than 95% pure and most preferably greater than 99% pure with respect to contaminating proteins and are essentially free of host cell nucleic acids. The proteins are delivered in a volume sufficient to cover the wound. A therapeutically effective amount sufficient to accelerate the rate of appearance and increase the number of new fibroblasts in the wound space, and to stimulate DNA synthesis in and collagen deposition by those fibroblasts, will typically be in the range of about 0.1–10.0 $\mu$g per cm$^2$ of wound area, preferably about 0.5–5.0 $\mu$g/cm$^2$ of wound area, depending upon the characteristics of the wound. The therapeutic compositions according to the present invention may be reapplied at one- to several-day intervals. Treatment will generally include administration of the above-described doses on a daily basis for between 5 and 30 days, although the particular treatment regimen will be determined by the nature of the wound.

Therapeutic compositions according to the present invention comprise the proteins described herein in combination with a suitable carrier or diluent. Typically, the proteins described herein will be used in a concentration of about 10 to 100 $\mu$g/ml of total volume, although concentrations in the range of 1 $\mu$g/ml to 1000 $\mu$g/ml may be used. Suitable carriers and diluents include water-based cellulose gels (e.g. Cellosize™, Dow Chemical Co.), biodegradable polymers, and aqueous creams, ointments and sprays. These compositions may further include adjuvants such as collagen or hyaluronic acid preparations, fibronectin, factor XIII, or other proteins or substances designed to stabilize or otherwise enhance the active therapeutic ingredient(s). Other stabilizers, antioxidants, or protease inhibitors may also be added. Alternatively, the proteins may be applied to wounds or wound dressings as aqueous solutions.

The therapeutic compositions of the present invention may also contain other pharmaceutically active ingredients, for example, heparin, which has been shown to accelerate the healing of thermal burns. Other growth factors, such as TGF-$\alpha$, TGF-$\beta$, EGF, basic FGF, acidic FGF, platelet factor 4, insulin or somatomedins may be combined with the PDGF-like proteins as generally disclosed by Antoniades et al. (WO 90/01331, U.S. Pat. No. 4,874,746) and Sundsmo et al. (EP 243,179). Antibiotics may also be included to keep the wound free of infection.

The following examples are offered by way of illustration, and not by way of limitation.

EXAMPLES

Restriction endonucleases and other DNA modifying enzymes were obtained from Bethesda Research Laboratories, New England Biolabs or Boehringer Mannheim Biochemicals and generally used according to the supplier's instructions.

Oligonucleotides were synthesized on an Applied Biosystems model 380A DNA synthesizer and purified by polyacrylamide gel electrophoresis. Oligonucleotides were labeled with gamma-$^{32}$P-ATP using protein kinase.

In vitro site-specific mutagenesis was performed by the two primer method, essentially as described by Zoller and Smith (*DNA* 3:479–488, 1984) using the universal second primer ZC87 (5' TCC CAG TCA CGA CGT 3') or by the one primer method (Zoller and Smith, *Nuc. Acids Res.* 10:6487–6500, 1982; Zoller and Smith, *Meth. Enzymology* 100:468–500, 1983).

General cloning procedures and methods for transforming *E. coli* are described by Maniatis et al. (*Molecular Cloning, A Laboratory Manual,* Cold Spring Harbor Laboratory, Cold Spring Harbor, N.Y., 1982). Yeast cells were transformed essentially as described by Beggs (*Nature* 275:104–108, 1978) and Hinnen et al. (*Proc. Natl. Acad. Sci. U.S.A* 75:1929–1933, 1978).

PDGF activity assays were performed generally according to published procedures (see, e.g., Murray et al., U.S. Pat. No. 4,845,075). The radioreceptor assay for PDGF was performed essentially as described by Bowen-Pope and Ross (*J. Biol. Chem.* 257:5161, 1982) using subconfluent monolayers of human diploid fibrobasts. Mitogenic activity was assayed by measurement of $^3$H-thymidine incorporation based on the method of Raines and Ross (*Meth. Enzymology* 109:749–773, 1985). Briefly, quiescent Swiss mouse 3T3 cells were obtained by plating cells at a density of 3×10$^5$ cells/ml in DMEM containing 10% fetal calf serum (FCS) in 96-well plates and allowing them to grow for 3–4 days. The medium was removed, and 180 µl of DMEM containing 1% FCS was added per well. Test samples serially diluted in 10 mM acetic acid/2.5 mg/ml rabbit serum albumin (20 µl sample volume) were added to the wells. The plates were incubated 20 hours at 37° C., and the medium was removed. 100 µl of DMEM containing 5% FCS and 2 µCi/ml $^3$H-thymidine was added to each well, and the plates are incubated an additional 3 hours at 37° C. The medium was aspirated off, the wells were washed with phosphate buffered saline (200 µl/well), and 100 µl of a 0.25% trypsin solution in PBS was added to each well. The plates were incubated at 37° C. until the cells detached (at least 10 minutes). The cells were harvested onto filters using an LKB Wallac 1295-001 Cell Harvester. Incorporated radioactivity was determined by counting the filters in an LKB Betaplate scintillation counter. Results were compared to those obtained using a known PDGF standard.

Specific receptor binding of PDGF-like proteins is measured in a binding competion assay. Test samples are diluted and added to SK5 fibroblasts in 24-well trays. The cells are incubated for two hours in the presence of 1 ng/ml $^{125}$I-BB (using a BB mutant containing tyrosine at position 23). The ability of the test sample to compete with the labeled ligand is compared to a standard curve generated with native BB.

Chemotactic activity of PDGF-like proteins is assayed as generally described by Seppa at al. (*J. Cell. Biol.* 92, 584–588, 1982), incorporated herein by reference. Test solutions are placed in Boyden chambers and covered with 8 µm-pore-size polycarbonate filters coated with gelatin. 0.8 ml of a cell suspension (~3×10$^5$ cell/ml) is added to the top compartment of each chamber. The chambers are incubated at 37° C. for 4 hours in a humidified atmosphere of 5% CO$_2$ in air. The filters are then removed, and the cells are fixed and stained. Migrated cells are visualized by microscopy and counted.

Example 1

Codon-Optimized B-chain Expression Construction

Figure 3:
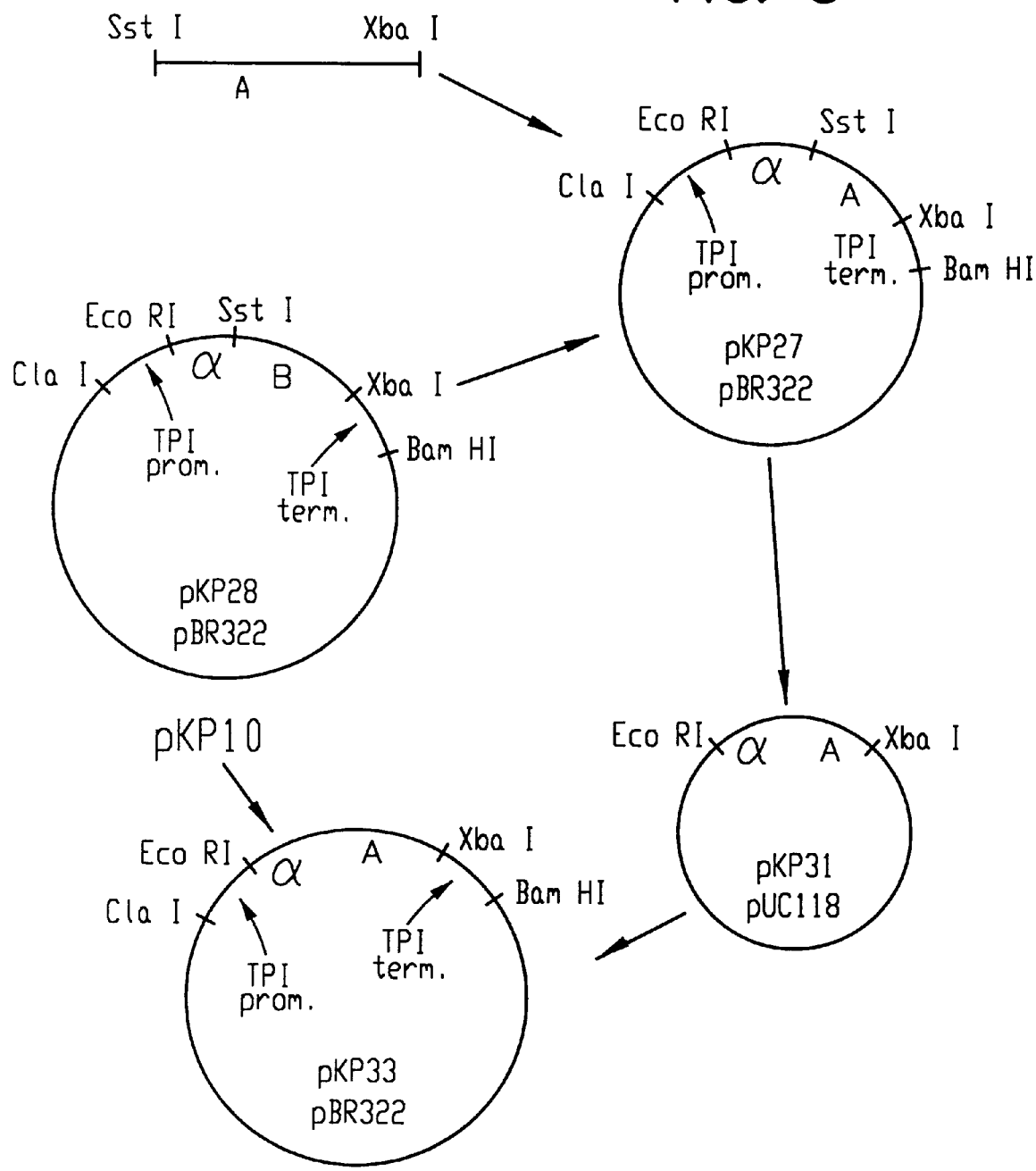
FIG. 3 illustrates the assembly of a PDGF A-chain expression unit.
Figure 4:
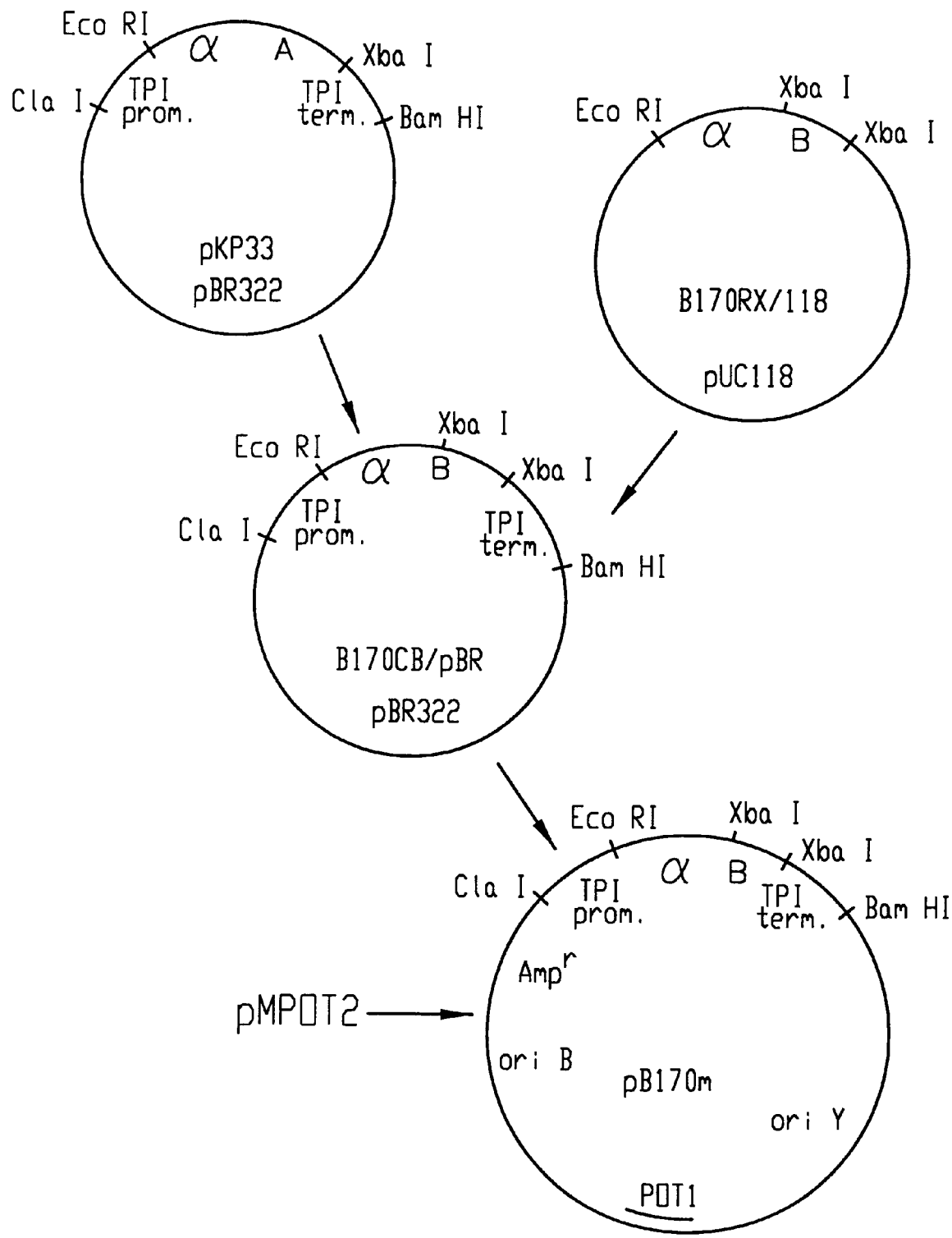
FIG. 4 illustrates the construction of a PDGF B-chain expression vector.

DNA sequences encoding the alpha-factor pre-pro and PDGF B-chain were modified to contain yeast-optimal codons and to encode wild-type alpha-factor pre-pro as well as authentic human B-chain. Construction of the optimized expression unit is illustrated in FIGS. 2–4.

A codon-optimized alpha-factor pre-pro sequence was obtained from an expression vector containing the gene for the insulin analog B(1-29)-Ala-Ala-Lys-A(1-21) (Harkussen et al., EP 163,529). An Eco RI-Xba I fragment comprising the alpha-factor pre-pro and insulin sequences was cloned into Eco RI, Xba I digested pUC118 (obtained from J. Vieira and J. Messing, Waksman Institute of Microbiology, Rutgers, Piscataway, N.J.; described by Vieira and Messing, *Meth. Enzymology* 153:311, 1987), and single-stranded template DNA was prepared. This template was then mutagenized according to the two-primer method (Zoller and Smith, *DNA* 3:479–488, 1984) using the mutagenic oligonucleotide ZC862 (5' CGA ATC TTT TGA GCT CAG AAA CAC C 3'). The mutagenesis resulted in the creation of an Sst I site at the 3' end of the alpha-factor pre-pro. A correctly altered plasmid was selected and designated pKP23. The pre-pro sequence was excised from pKP23 by digestion with Eco RI and Sst I, and the leader fragment was subcloned into Eco RI and Sac I-cut pIC19H (Marsh et al., *Gene* 32:481–486, 1984). The resultant plasmid was designated pKP24 (FIG. 2).

The human B-chain sequence was obtained from plasmid pB12. (Plasmid pB12 is disclosed by Murray et al., U.S. Pat. No. 4,845,075. Briefly, pB12 comprises a DNA sequence encoding human PDGF B-chain operatively linked to the *S. cerevisiae* TPI1 promoter, MFα1 pre-pro sequence and TPI1 terminator.) As shown in FIG. 2, pB12 was digested with Eco RI and Xba I and the α-factor/B-chain fragment was recovered. Plasmid pKP10, comprising the TPI1 promoter—alpha-factor—B-chain—TPI1 terminator expression unit of pSB1 (Hurray et al., U.S. Pat. No. 4,845,075) inserted into a pBR322 vector lacking an Eco RI site, was digested with Eco RI and Xba I to remove the α-factor/B-chain sequence. The pB12 α-factor/B-chain sequence was then inserted into the pKP10 expression unit. The resultant plasmid was designated pKP26.

The yeast codon-optimized alpha-factor sequence was then introduced into the expression unit (FIG. 2). Plasmid pKP26 was cut with Eco RI and Sst I to remove the α-factor sequence. The codon-optimized α-factor sequence was then removed from pKP24 as an Eco RI-Sst I fragment and joined to the linearized pKP26. The resultant vector was designated pKP28.

The Sst I site that had been introduced into the alpha-factor pre-pro sequence to facilitate vector construction was then removed to restore the wild-type coding sequence.

Plasmid pKP28 was digested with Eco RI and Xba I, and the alpha-factor—B-chain fusion sequence was recovered. This fragment was cloned into pUC118 and single-stranded template DNA was isolated. The template was mutagenized by the two primer method using the mutagenic oligonucleotide ZC1019 (5' ACC CAA GGA TCT CTT GTC CAA AGA AAC ACC TTC TTC 3'). A correctly mutagenized plasmid was designated pKP32 (FIG. 2).

In parallel constructions, the codon-optimized A-chain sequence from plasmid pA7 (Hurray et al., U.S. Pat. No. 4,889,919) was combined with the codon-optimized alpha-factor pre-pro sequence (FIG. 3). The pA7 A-chain sequence was isolated as a Sst I-Xba I fragment and inserted into Sst I, Xba I-cut pKP28 to construct pKP27. Plasmid pKP27 was digested with Eco RI and Xba I, and the alpha-factor—A-chain fragment was cloned into pUC118. Mutagenesis, using the oligonucleotide ZC1018 (5' TTC GAT AGA TCT CTT GTC CAA AGA AAC ACC TCC TTC 3'), was carried out according to standard procedures to remove the Sst I site and restore the wild-type alpha-factor sequence. The corrected plasmid was designated pKP31. Plasmid pKP31 was digested with Eco RI and Xba I, and the alpha-factor—A-chain fragment was joined to Eco RI, Xba I cut pKP10. The resultant vector, designated pKP33, contained the entire expression unit.

The B-chain sequence was then codon-optimized. An internal Bgl II-Sph I fragment of the B-chain sequence of pKP32 was replaced with a sequence assembled from the oligonucleotides shown in Table 1. The resultant construct was designated B170RX/118 (FIG. 2). The Bgl II-Sph I fragment of this plasmid was cloned into an M13 page vector and sequenced to verify the construction. Plasmid B170RX/118 was digested with Eco RI and partially digested with Xba I to isolate the α-factor—B-chain fragment. This fragment was joined to the Eco RI-Xba I vector fragment of pKP33 to construct B170CB/pBR. The expression cassette was isolated from B170CB/pBR as a Cla I-Bam HI fragment and cloned into Cla I, Bam HI-digested pMPOT2 (ATCC 67788). The pMPOT2-based expression vector containing the fully optimized B-chain expression unit was designated pB170m (FIG. 4).

To construct an expression unit for the mutant B-chain, the mutagenized fragment was removed from the M13mp18 vector as an Xba I fragment. A plasmid comprising the B170 expression unit (Cla I-Bam HI fragment) in pIC19R (designated B170/19R) was digested with Xba I, and the large fragment was recovered. The mutagenized B-chain fragment was then joined to the large pIC19R/B170 fragment to restore the entire coding sequence, resulting in an expression unit of TPI1 promoter, codon-optimized alpha-factor pre-pro, mutagenized B-chain coding sequence and TPI1 terminator. The resulting construct was transformed into E. coli DH5α and colonies were screened using kinased ZC1694. A correct plasmid was designated B172/19R.

A yeast expression vector was then assembled. The B172 expression unit was isolated from B172/19R as a Cla I-Bam HI fragment and joined to Cla I, Bam HI-digested pMPOT2. Restriction analysis of the resulting construct indicated that the expression unit was not properly joined to the vector. The construct was then digested with Xba I, and the 255 bp mutagenized B-chain fragment was recovered. The 255 bp fragment was again inserted into the B170 expression unit as described above, and the resulting B172 expression unit was isolated and joined to Cla I, Bam HI-digested pMPOT2. The resulting construct was transformed into E. coli DH5α. A clone having the desired structure was identified by restriction analysis and screening with labeled oligonucleotide ZC1694 and designated pB172M.

Plasmid pB172M was transformed into S. cerevisiae strain ZM137 (a/α leu2-3, 112/leu2-3, 112 his4-580/+ pep4-3/pep4-3 Δtpi1::LEU2/Δtpil::LEU2 cir°/cir°). Transformants were cultured in glucose medium, and 600 ml was inoculated into 50 liters of medium containing 7.5 g/L yeast extract, 14.0 g/L (NH$_4$)$_2$SO$_4$, 2.7 g/L KH$_2$PO$_4$, 25 ml vitamin solution (0.05 mg/ml biotin, 0.5 mg/ml thiamine) and 5 ml antifoam (polypropylene glycol; Aldrich, Milwaukee, Wis.). To the medium were added 3.5 L of 2M NH$_4$OH and 5.5 L of glucose solution (58.7% glucose containing 5.87 ml/L trace element solution [215.5 mg/L MnSO$_4$.1H$_2$O, 283.6 mg/L FeSO$_4$.7H$_2$O, 28.1 mg/L CuSO$_4$.5H$_2$O] and citric acid [1 g/kg glucose]). The cells were cultured at 30° C. with agitation. After 21 hours, 3.1 L

TABLE 1

| | Sequence (5'→3') |
|---|---|
| ZC886 | GGCCACCATGTGTTGAAGTTCAAAGATGCTCGGGTTGTTGTAACAACAGAAACGTTCAATG |
| ZC887 | TCGACATTGAACGTTTCTGTTGTTACAACAACCCGAGCATCTTTGAACTTCAACACATG |
| ZC888 | GATCTCTAGAAGATTGATCGACAGAACCAACGCCAACTTCTTGGTTT |
| ZC889 | GTGGCCAAACCAAGAAGTTGGCGTTGGTTCTGTCGATCAATCTTCTAGA |
| ZC907 | CGTTAGAAAGAAGCCAATCTTCAAGAAGGCTACCGTTACCCTCGAGGACCACTTGGCATG |
| ZC908 | TCGACCAACCCAAGTTCAATTGCGGCCGGTTCAAGTGCGCAAGATCGAAAT |
| ZC909 | CTAACGATTTCGATCTTGCGCACTTGAACCGGCCGCAATTGAACTTGGGTTGG |
| ZC910 | CCAAGTGGTCCTCGAGGGTAACGGTAGCCTTCTTGAAGATTGGCTTCTTT |

Example 2

Replacement of Arginine-32

To convert the codon for arginine at amino acid position 32 of the B-chain to a proline codon, the 255 bp Xba I fragment from pB170m was cloned into the Xba I site of the phage vector M13mp18. Single-chain template DNA was prepared and mutagenized by the one-primer method using oligonucleotide ZC1694 (5' GGC GTT GGT TGG GTC GAT CAA T 3'). Plaques were screened with oligonucleotide ZC1694 that had been kinased in the presence of γ$^{32}$P-ATP. Two positive plaques were sequenced and found to contain the desired mutagenized sequence.

of 2M NH$_4$OH and 5.5 L of glucose solution were added. After approximately 41 hours of fermentation, 3.0 L of glacial acetic acid and 60 ml of phosphoric acid were added. After an additional two hours, the cells and medium were separated using a Kros Flo II 0.2 μm filter (Microgon). The medium was then concentrated about sixty-fold using a 10 kd membrane filter (Amicon S10Y10 spiral cartridge; Amicon, Danvers, Mass.).

The recombinant Arg-32 PDGF BB was purified from the concentrated fermentation broth. The concentrate was frozen, thawed and adjusted to 1M acetic acid. This solution was centrifuged for 60 minutes at 16,000×g, 420 C. The supernatant was recovered and applied to a 30 ml S-Sepharose (Pharmacia) column at 4 ml/min. The column was washed with 1M acetic acid, then eluted with a step gradient of pH 4.5 ammonium acetate (0.1M, 0.5M and 1.0M) in 1M acetic acid. The 1M acetic acid acid eluate was dialyzed against 1M acetic acid, then lyophilized. The lyophilized material was resuspended in 1 ml of 1M acetic acid, 0.25M ammonium acetate pH 4.5. The resulting solution was applied to a 200 ml column of Sephadex G-50 (Pharmacia) at a flow rate of 0.15 ml/min., and the column was eluted with the same buffer. Peak fractions were diluted 1:3 in 1M acetic acid, and 1 ml of the solution was fractionated by FPLC on a Mono S column (Pharmacia). The column was eluted with a gradient of 0–1M ammonium acetate pH 4.5 in 1M acetic acid. Under these conditions, PDGF eluted between 0.6M and 0.8M ammonium acetate. The FPLC peak was applied to a Vydac C-4 HPLC column (The Separations Group, Hesperia, Calif.) at 1 ml/min. Separation was achieved using a 2%/min. gradient of acetonitrile in 0.1% trifluoroacetic acid. PDGF eluted at 40–50% acetonitrile. The purified protein was lyophilized for storage. Throughout purification, PDGF content was monitored by radio-receptor assay and gel electrophoresis. Overall recovery of PDGF was estimated at 60%.

Mitogenic activity of the purified protein was determined in a standard assay of $^3$H-thymidine incorporation. Results indicated a protein concentration of 77 µg/ml by activity, compared to 95 µg/ml by quantitative amino acid analysis.

Example 3

Replacement of Arginine-28

To replace the arginine residue at position 28 with a serine residue, the 255 bp Xba I fragment from pB170m was cloned into the Xba I site of M13mp18. Single-stranded template DNA was prepared and mutagenized by the one-primer method using oligonucleotide ZC1695 (5' TGT CGA TCA AAG ATC TAG AGG AT 3'). Plaques were screened with $^{32}$P-labeled ZC1695.

A sequence-confirmed mutagenized clone is digested with Xba I, and the PDGF fragment is recovered and cloned into B170/19R as described in Example 2. A correctly oriented clone is identified by restriction analysis. A correct clone is digested with Cla I and Bam HI to isolate the PDGF expression cassette, which is then cloned in pMPOT2 to construct a yeast expression vector for Ser-28 PDGF BB.

Example 4

Stimulation of Would Repair

The effectiveness of PDGF B-chain homodimer (prepared essentially as described in Example 2 using cells transformed with pB170m) in stimulating wound repair was studied in normal and diabetic mice. This animal wound model used the congenitally diabetic C57BL/KsJ-dbm (db/db) mouse (Jackson Laboratories, Bar Harbor, Me.). These animals are hyperglycemic and insulin-resistant. Heterozygote litter mates (not expressing the diabetic phenotype) were used as controls. Typically, untreated, 1.5×1.5 cm full-thickness skin wounds on the nondiabetic control mice completely close and heal by 14 days after surgery. The area decreases approximately 85% by contraction and the remaining 15% closes by formation of granulation tissue and epithelial migration. In contrast, untreated wounds on the diabetic mice do not decrease significantly in size in 14 days, nor do they develop much granulation tissue in that time. The wounds on the diabetic mice eventually heal, but the process takes 8–12 weeks. The cause of the healing impairment in these animals is not known.

1.5 cm×1.5 cm full-thickness skin wounds were made on the backs of anesthetized animals and covered with Opsite semi-permeable dressings (Smith and Nephew Medical, Hassillon, Ohio). Immediately after wounding and daily for four days thereafter, 0.1 ml of the treatment mixture was injected through the dressing onto the wound bed. The growth factors were mixed with 0.25% mouse serum albumin (MSA) in phosphate-buffered saline for administration. The edges of the wounds were traced on days 0, 1, 2, 3, 4, 7, 10, 15 and 21 after surgery for calculation of open wound area. Ten or 21 days after injury the animals were sacrificed and the wounds were taken for histological and biochemical analysis. Each wound was scored without knowledge of its treatment group by three investigators. Scores were assigned on the basis of the presence/absence, thickness, cellularity and maturity of granulation tissue and the degree of epithelial migration from the wound edge.

Results of the study indicated that the treatment with PDGF-BB homodimer enhanced wound healing in the diabetic animals. Injection of 0.25% MSA onto the wound bed did not affect the rate of healing or the development of granulation tissue in the diabetic mice. In the margin of a wound treated with 0.25% MSA 10 days after wounding there was a thin band of loosely organized cells and connective tissue under the migrating epithelium, but at the center of the wound bed there were only patchy accumulations of cells. In contrast, administration of 5 µg of recombinant PDGF-BB for 5 days stimulated the formation of granulation tissue in the diabetic mice by 10 days after injury. The band of granulation tissue beneath the epithelium was much thicker and more vascular than in the corresponding control (MSA) mice. There was no difference in the wound size at 10 days between the MSA and PDGF-BB treated wounds.

A second series of experiments tested the efficacy of recombinant BB in a polyethylene glycol (PEG) carrier in the same animal model. Full-thickness skin wounds (1.5×1.5 cm) were made in the paravertebral region of the anesthetized animals and covered with Opsite. Immediately after wounding and daily for four or nine days thereafter, 0.1 ml of the treatment mixture was injected through the dressing and onto the wound bed. Diabetic test animals received recombinant BB (1 µg or 10 µg) in 5% PEG (Carbowax PEG 8000, USP grade, Union Carbide, Danbury, Conn.) in phosphate buffered saline. Controls received 5% PEG alone. The edges of the wounds were traced onto glass slides and the wound areas were determined using computerized planimetry. Ten or 21 days after wounding the wounds were analyzed for the degree of closure and contraction. Results are shown in Table 2.

TABLE 2

| Treatment | % Closure (n) | % Contraction (n) |
|---|---|---|
| 10 Day Evaluation | | |
| PEG × 5 | 40.71 ± 4.78 (20) | 16.56 ± 2.96 (20) |
| 1 µg BB × 5 | 46.77 ± 5.86 (20) | 22.75 ± 4.28 (20) |
| PEG × 5 | 28.52 ± 1.57 (22) | 16.10 ± 1.45 (22) |
| 10 µg BB × 5 | 41.59 ± 2.48 (22)* | 24.96 ± 1.67 (22)* |
| 21 Day Evaluation | | |
| PEG × 5 | 77.47 ± 6.25 (10) | 59.74 ± 5.58 (10) |
| 1 µg BB × 5 | 76.34 ± 5.96 (10) | 57.21 ± 6.12 (10) |

TABLE 2-continued

| Treatment | % Closure (n) | % Contraction (n) |
|---|---|---|
| PEG × 5 | 43.04 ± 4.72 (32) | 28.13 ± 3.44 (32) |
| 10 μg BB × 5 | 65.40 ± 5.38 (34)* | 35.19 ± 3.71 (34) |
| PEG × 10 | 62.25 ± 8.56 (11) | 47.43 ± 7.11 (11) |
| 1 μg BB × 10 | 85.69 ± 4.91 (12) | 54.97 ± 5.17 (12) |
| PEG × 10 | 57.67 ± 4.35 (39) | 39.46 ± 3.31 (39) |
| 10 μg BB × 10 | 85.22 ± 3.22 (44)* | 47.16 ± 2.05 (44)* |

*$p < 0.05$, T test

Although the foregoing invention has been described in some detail for purposes of clarity of understanding, various modifications may be made without deviating from the spirit and scope of the invention. Accordingly, the invention is not to be limited except as by the appended claims.

What is claimed is:

1. A PDGF B-chain polypeptide characterized by a substitution or deletion at an amino acid position selected from the group consisting of position 27, position 28, position 32, position 79, position 80 and position 81 of native B-chain, wherein said polypeptide has increased protease resistance compared to protease resistance of wild-type PDGF-B chain polypeptide.

2. A PDGF B-chain polypeptide according to claim 1, wherein an amino acid selected from the group consisting of proline, serine, tryptophan, glutamine, histidine, methionine and asparagine is substituted for arginine-32.

3. A PDGF B-chain polypeptide according to claim 1, wherein an amino acid selected from the group consisting of proline serine, tryptophan, glutamine, histidine, methionine and asparagine is substituted for arginine-28.

4. A PDGF-like protein comprising a first B-chain polypeptide disulfide bonded to an A-chain polypeptide or another B-chain polypeptide, wherein said first B-chain polypeptide is characterized by a substitution or deletion at an amino acid position selected from the group consisting of position 27, position 28, position 32, position 79, position 80 and position 81 of native B-chain, wherein said protein has increased protease resistance compared to protease resistance of native PDGF.

5. A PDGF-like protein according to claim 4 in combination with a physiologically acceptable carrier or diluent.

6. A PDGF-like protein according to claim 4 wherein said first B-chain polypeptide contains an amino acid other than arginine or lysine at position 32.

7. A PDGF-like protein according to claim 6, wherein said amino acid is selected from the group consisting of proline, serine, tryptophan, glutamine, histidine, methionine and asparagine.

8. A PDGF-like protein according to claim 6, wherein said amino acid is proline.

9. A PDGF-like protein according to claim 6, wherein said first B-chain polypeptide is disulfide bonded to another B-chain polypeptide.

10. A PDGF-like protein according to claim 6, wherein said first B-chain polypeptide is disulfide bonded to an A-chain polypeptide.

11. A PDGF-like protein according to claim 4, wherein said first B-chain polypeptide contains an amino acid other than arginine or lysine at position 28.

12. A PDGF-like protein according to claim 11, wherein said amino acid is selected from the group consisting of proline, serine, tryptophan, glutamine, histidine, methionine and asparagine.

13. A PDGF-like protein according to claim 11, wherein said amino acid is serine.

14. A PDGF-like protein according to claim 11, wherein said first B-chain polypeptide is disulfide bonded to another B-chain polypeptide.

15. A PDGF-like protein according to claim 11, wherein said first B-chain polypeptide is disulfide bonded to an A-chain polypeptide.

* * * * *